(12) United States Patent
Stergiopoulos et al.

(10) Patent No.: US 7,854,701 B2
(45) Date of Patent: Dec. 21, 2010

(54) NON-INVASIVE MONITORING OF INTRACRANIAL DYNAMIC EFFECTS AND BRAIN DENSITY FLUCTUATIONS

(75) Inventors: Stergios Stergiopoulos, Toronto (CA); Miroslaw Wrobel, Toronto (CA)

(73) Assignee: Stergios Stergiopoulos, Toronto, Ontario (CA)

( * ) Notice: Subject to any disclaimer, the term of this patent is extended or adjusted under 35 U.S.C. 154(b) by 1833 days.

(21) Appl. No.: 10/898,208

(22) Filed: Jul. 26, 2004

(65) Prior Publication Data
US 2005/0033171 A1    Feb. 10, 2005

Related U.S. Application Data

(60) Provisional application No. 60/489,491, filed on Jul. 24, 2003.

(51) Int. Cl.
*A61B 8/00* (2006.01)
*G01H 1/00* (2006.01)
*H04R 1/28* (2006.01)
*G01N 29/00* (2006.01)

(52) U.S. Cl. .................. 600/442; 600/437; 600/438; 600/449; 600/451; 73/584; 73/586; 73/587; 73/589

(58) Field of Classification Search ......... 600/437–461; 73/584–648
See application file for complete search history.

(56) References Cited

U.S. PATENT DOCUMENTS

| 4,669,482 | A | * | 6/1987 | Ophir | 600/449 |
|---|---|---|---|---|---|
| 4,703,758 | A | * | 11/1987 | Omura | 600/485 |
| 4,930,511 | A | * | 6/1990 | Rossman et al. | 600/449 |
| 4,971,061 | A | * | 11/1990 | Kageyama et al. | 600/438 |
| 5,074,310 | A | * | 12/1991 | Mick | 600/561 |
| 5,117,835 | A | * | 6/1992 | Mick | 600/561 |
| 5,388,583 | A | * | 2/1995 | Ragauskas et al. | 600/451 |
| 5,951,476 | A | * | 9/1999 | Beach | 600/437 |
| 5,951,477 | A | * | 9/1999 | Ragauskas et al. | 600/438 |
| 6,086,533 | A | * | 7/2000 | Madsen et al. | 600/438 |
| 6,117,089 | A | * | 9/2000 | Sinha | 600/561 |
| 6,387,051 | B1 | | 5/2002 | Ragauskas et al. | |
| 6,475,147 | B1 | * | 11/2002 | Yost et al. | 600/438 |
| 6,517,487 | B1 | | 2/2003 | Mazess et al. | |
| 6,547,734 | B2 | * | 4/2003 | Madsen et al. | 600/438 |
| 6,731,976 | B2 | * | 5/2004 | Penn et al. | 600/544 |

(Continued)

FOREIGN PATENT DOCUMENTS

CA    2391123    1/2003

(Continued)

*Primary Examiner*—Ruth S Smith
*Assistant Examiner*—Joseph Santos
(74) *Attorney, Agent, or Firm*—Freedman & Associates

(57) ABSTRACT

The present invention relates to a method and apparatus for non-invasive monitoring of brain density variations. At least two ultrasonic pulses having different frequencies are provided into the brain for transmission therethrough. The reflected ultrasonic pulses are then sensed and the sensed signal data are then processed for determining at least two phase differences between the phases of the at least two reflected ultrasonic pulses and the phases of the at least two provided ultrasonic pulses. A phase of at least a beat frequency is determined in dependence upon the at least two phase differences. Data indicative of a brain density variation are determined based on the at least two phase differences and the at least a beat frequency.

21 Claims, 13 Drawing Sheets

U.S. PATENT DOCUMENTS

| | | | |
|---|---|---|---|
| 6,740,048 B2 * | 5/2004 | Yost et al. | 600/561 |
| 6,875,176 B2 * | 4/2005 | Mourad et al. | 600/442 |
| 2003/0074953 A1 * | 4/2003 | Glaser et al. | 73/32 A |
| 2003/0167848 A1 * | 9/2003 | Glaser et al. | 73/597 |
| 2004/0099815 A1 * | 5/2004 | Sfez et al. | 250/492.1 |

FOREIGN PATENT DOCUMENTS

| | | |
|---|---|---|
| CA | 2391123 A1 * | 1/2003 |
| WO | WO 02/10738 | 2/2002 |

* cited by examiner $$\Delta\tau \approx \frac{2(0.055\,m)}{1550\,{}^m\!/\!{}_s} = 70.97\,\mu s\ (\approx 710\,points)$$

NON-INVASIVE MONITORING OF INTRACRANIAL DYNAMIC EFFECTS AND BRAIN DENSITY FLUCTUATIONS

This application claims benefit from U.S. Provisional Application No. 60/489,491 filed Jul. 24, 2003.

FIELD OF THE INVENTION

This invention relates to monitoring of intracranial pressure and brain density variations and in particular to a method and apparatus for non-invasive monitoring of intracranial pressure and brain density variations.

BACKGROUND OF THE INVENTION

Methods and devices for monitoring IntraCranial Pressure (ICP) and brain density variations are highly valued for diagnosis and assessment of various ailments including head injuries, hemorrhage, variations of blood flow in the skull due to drug effects, changes in brain temperature and variations in metabolism and stress. Elevated ICP is a pathological condition of a patient and an indicator of neurological damage and illness. Numerous pathological conditions cause the matter within the skull to increase, but the inability of the skull to expand significantly causes the ICP to increase exponentially with increasing matter. A primary concern caused by an elevated ICP is brain herniation. The brain herniation is a condition in which a portion of the brain is displaced due to increased pressure—resulting in progressive damage to the brain—and is ultimately fatal. Usually, the brain herniation is a result of cerebral edema, which is the medical term for the condition of a swollen brain, usually caused by head injury. Elevated ICP is also caused by increased brain water content or other metabolic, traumatic and infectious conditions such as hypoxia, ischemia, brain hemorrhage, tumor and meningitis. Hypoxia occurs due to a lack of oxygen supplied to the brain, usually caused by cardiac arrest, leading to brain edema. Ischemia is the condition of deprivation of blood flow to the brain and leads to stroke because glucose and oxygen are not supplied to the brain. Ischemia is usually caused by formation of a blood clot (thrombus) and leads to the death of parts of the brain or ultimately of all the brain (cerebral infarction). Intracerebral hemorrhage is an increase in blood volume within the cranium, which is directly correlated with an increase in ICP. The main cause of intracerebral hemorrhage is a ruptured blood vessel in the brain resulting from a blow to the head or due to hypertension. The added mass of a brain tumor also causes an increase in ICP. In fact, an increase in ICP occurring without any head injury is often a sign of the presence of a brain tumor. Meningitis is a bacterial or viral infection of the meninges, a three-layer membrane surrounding the brain and spinal cord. Meningitis causes the meninges to swell and press against the skull and the brain. As a result, an intense pressure build up occurs notably raising the ICP. If not treated rapidly, meningitis leads to herniation. Therefore, measurement of the ICP is significant for detecting various neurological conditions. Furthermore, early detection of ICP variations is recognized as an important tool in improving a patient's condition or, ultimately, saving a patient's life. As well, monitoring the ICP is critical for identifying changes in a patient's pathological state.

At the present time accurate measurements of the ICP are only obtained using invasive techniques. However, the invasive techniques involve exposing brain tissue increasing the risk of infection, hemorrhage, and leakage of cerebral spinal fluid and, therefore, increasing the possibility of further aggravating a patient's condition.

Current state of the art non-invasive techniques for monitoring the ICP are not able to provide the accuracy, availability and usefulness of the invasive techniques. Non-invasive techniques include Computed Tomography (CT), Magnetic Resonance Imaging (MRI), Positron Emission Tomography (PET), Single Photon Emission Computed Tomography (SPECT), Transcranial Doppler ultrasonography (TCD), Transcranial Near-Infrared Spectroscopy (TNIRS), Ophthalmodynamomery (OMD), and impedance audiometry. Other non-invasive techniques have been recently disclosed in U.S. Pat. No. 5,951,477 issued Sep. 14, 1999 to Ragauskas et al. and in U.S. Pat. No. 5,388,583 issued Feb. 14, 1995 to Ragauskas et al. These techniques provide time delay estimation for measuring brain density variations—with the ICP variations being directly related thereto—by probing a patient's brain with ultrasound pulses of a specific frequency band. However, these techniques are inaccurate, ignoring dependency of brain density variations on a wide range of frequencies, and, therefore, disregarding information essential to accurately account for dispersive properties of a human brain.

It would be advantageous to provide a method and apparatus for non-invasive monitoring of brain density variations that is capable of replacing the invasive techniques. Furthermore, it would be highly advantageous to provide an apparatus for non-invasive monitoring of brain density variations in real time that is portable and easy to use.

SUMMARY OF THE INVENTION

It is, therefore, an object of the invention to provide a method and apparatus for non-invasive monitoring of the ICP.

It is yet further an object of the invention to provide a method and apparatus for non-invasive monitoring of the ICP in real time that is portable and easy to use.

In accordance with the present invention there is provided a method for non-invasive monitoring density variations of a medium substantially confined within at least a solid boundary comprising:
a) providing at least two ultrasonic pulses having different frequencies into the medium for transmission therethrough;
b) sensing the at least two ultrasonic pulses after traveling through the medium and providing a receive signal in dependence thereupon;
c) converting the receive signal into digital receive signal data;
d) processing the digital receive signal data for determining at least two phase differences between the phases of the at least two sensed ultrasonic pulses and the phases of the at least two provided ultrasonic pulses;
e) determining phase of at least a beat frequency in dependence upon the at least two phase differences; and,
f) determining data indicative of a density variation of the medium based on the at least two phase differences and the at least a beat frequency.

In accordance with the present invention there is further provided an apparatus for non-invasive monitoring density variations of a medium substantially confined within at least a solid boundary comprising:
an ultrasonic pulse generator for generating at least two ultrasonic pulses having different frequencies;
a transmitter in signal communication with the ultrasonic pulse generator for coupling the at least two ultrasonic pulses into the medium for transmission therethrough;

at least a sensor for sensing the at least two ultrasonic pulses after traveling through the medium and for providing a receive signal in dependence thereupon;

an analog-to-digital converter in signal communication with the at least a sensor for converting the receive signal into digital receive signal data;

a processor in communication with the ultrasonic pulse generator and the analog-to-digital converter, the processor for:

a) providing at least a control signal to the ultrasonic pulse generator indicative of at least a parameter of the at least two ultrasonic pulses;

b) processing the digital receive signal data for determining at least two phase differences between the phases of the at least two sensed ultrasonic pulses and the phases of the at least two provided ultrasonic pulses;

c) determining at least a beat frequency phase in dependence upon the at least two phase differences; and, d) determining data indicative of a density variation based on the at least two phase differences and the at least a beat frequency.

In accordance with the present invention there is yet further provided an apparatus for non-invasive monitoring of brain density variations comprising:

an ultrasonic pulse generator for generating at least two ultrasonic pulses having different frequencies;

a transmitter in signal communication with the ultrasonic pulse generator for coupling the at least two ultrasonic pulses into the brain for transmission therethrough;

a sensor array probe for sensing the at least two ultrasonic pulses after traveling through the medium and for providing a receive signal in dependence thereupon;

an analog-to-digital converter in signal communication with the sensor array for converting the receive signal into digital receive signal data;

a processor in communication with the ultrasonic pulse generator, the analog-to-digital converter, and the sensor array, the processor for:

a) providing at least a control signal to the ultrasonic pulse generator indicative of at least a parameter of the at least two ultrasonic pulses;

b) performing beam steering for detecting the at least two ultrasonic pulses;

c) processing the digital receive signal data for determining at least two phase differences between the phases of the at least two sensed ultrasonic pulses and the phases of the at least two provided ultrasonic pulses;

d) determining at least a beat frequency phase in dependence upon the at least two phase differences;

e) determining at least a density variation based on the at least two phase differences and the at least a beat frequency; and, f) repeating the steps a) to e) while varying the frequencies of the at least two ultrasonic pulses.

BRIEF DESCRIPTION OF THE FIGURES

Exemplary embodiments of the invention will now be described in conjunction with the following drawings, in which.

DETAILED DESCRIPTION OF THE INVENTION

The method and apparatus for non-invasive monitoring of brain density variations according to the invention utilizes ultrasonic waves to measure density variations in a brain. Various pathological conditions of the brain are related to an increase of mass within a substantially same volume of a skull resulting in an increase of the brain density, which is directly related to an increase in the ICP. Brain density variations are recorded by monitoring changes of the velocity of sound within the brain. The velocity of sound within a medium such as the brain is dependent on a number of parameters, including the state of the propagation properties of the medium. The brain is primarily composed of a liquid medium with numerous organic substances dissolved therein. The equation of the velocity of sound in a homogeneous liquid medium is given by:

$$c(f) = \sqrt{\frac{K(f)}{\rho}} \tag{1}$$

where c is the velocity of sound, f is frequency of the sound, $K(f)=\gamma B_T(f)$ is a constant for a same medium and frequency, $\gamma$ is a ratio of specific heat at constant pressure to that at constant volume, $\rho$ is density of the medium, and $B_T(f)$ is an isothermal bulk modulus of the medium. Of course, the fact that biological structures are heterogeneous complicate equation (1), but the important parameters affecting the velocity of sound are given in equation (1). The bulk modulus is frequency dependent and slightly temperature dependent. The main parameter affecting the velocity of sound is the density. In order to provide an accurate diagnosis by monitoring the brain density variations and correlating same with various pathological conditions of the brain necessitates determination of the brain density variations for a wide range of frequencies accounting for dispersive properties as expressed by equation (1).

Figure 1:
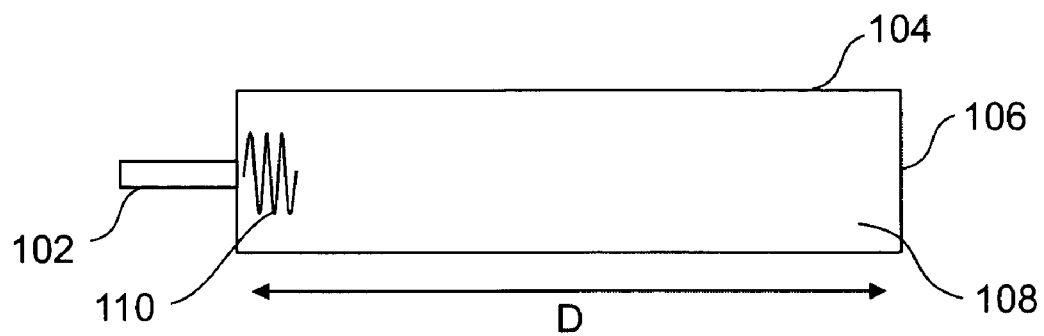
FIG. 1 is a simplified diagram schematically illustrating a system application of an apparatus for non-invasive monitoring of brain density variations according to the invention.

The aim of the method and apparatus for non-invasive monitoring of brain density variations according to the invention is to monitor variations of the density of a medium 108 confined within closed solid boundaries 104 such as a human brain surrounded by a skull, as shown in FIG. 1. In the following it will become apparent to those skilled in the art that the method and apparatus according to the invention is not limited for monitoring density variations in a brain, but is beneficially employable in numerous applications where it is desired to monitor the density variation of a medium confined within closed solid boundaries. For example, the non-invasive character of the method and apparatus according to the invention is highly beneficial in situations where it is not possible to provide an opening in a vessel for monitoring density variations or related pressure variations of a medium enclosed therein. The density variations are monitored by sending a sequence of ultrasonic pulses 110 through the matter 108 using, for example, a transmit-receive transducer 102. The ultrasonic pulses 110 are reflected at reflective surface 106, transmitted again through the matter 108 and sensed by the transmit-receive transducer 102. In case of a human brain, the ultrasonic pulses are sent into the brain through a small area of the skull near an ear—temporal bone—to ensure reception of a useful reflected signal. The traveling time $\Delta\tau$ of an acoustic wave propagating in the matter 108 shown in FIG. 1 is given by:

$$\Delta\tau = \frac{2D}{c} \tag{2}$$

Time delay determination is the basis for the analysis of properties of the contained medium due its simplicity, accurate measurements and numerous system solutions. A change of the parameters—D or c—in equation (2) results in a change in the acoustic wave's traveling time. The method and apparatus for non-invasive monitoring of brain density variations according to the invention also accounts for a change in D—the dimension of the skull—as will be explained below, while time estimation processing as disclosed in U.S. Pat. No. 5,951,477 and 5,388,583 accounts only for a variation in c. Monitored variations between successively transmitted and reflected acoustic pulse signals in the method and apparatus for non-invasive monitoring of brain density variations according to the invention are then directly related to variations in the density of the brain because variations in the velocity of sound are then directly related to variations in the density $\rho$. For a known brain density distribution of a healthy person, changes in the traveling time $\Delta\tau$ rare related to changes in temperature and pressure distribution. Thus, in the case of healthy brain conditions, the traveling time $\Delta\tau$ of successive ultrasound pulses remains substantially constant. Moreover, in cases of unhealthy brain conditions, a monitored variation of the traveling time $\Delta\tau$ corresponds to an abnormality. Investigating various pathological brain conditions and relating them to monitored variations of the traveling time $\Delta\tau$ in clinical trials enables non-invasive assessment of brain trauma or other pathological conditions of a patient's brain by recognizing a pattern of the monitored traveling time variation.

Figure 2:
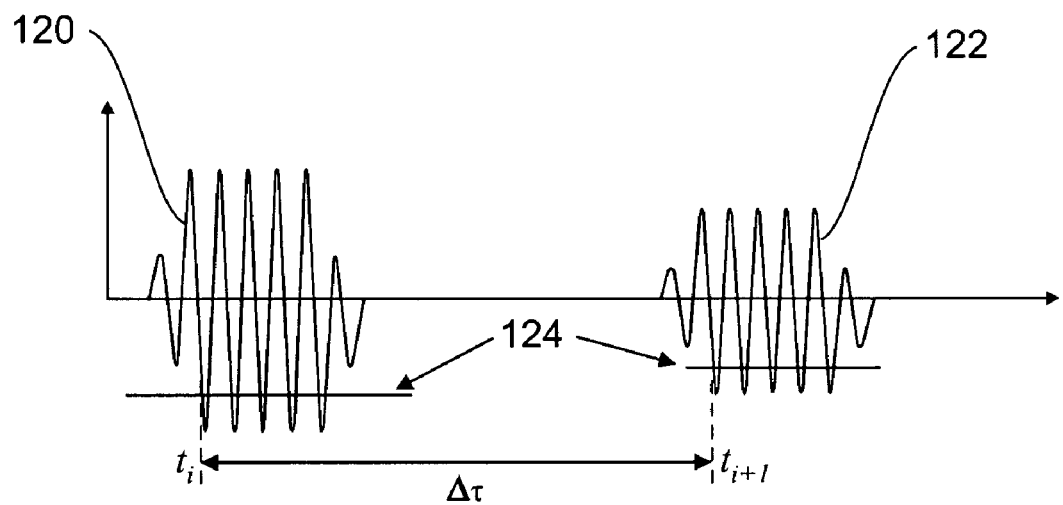
FIG. 2 is a simplified diagram schematically illustrating a trigger method.

The traveling time $\Delta\tau$ is determined using, for example, a trigger threshold method, as shown in FIG. 2, for determining $\Delta\tau$ between a transmit pulse 120 and a reflected pulse 122 using predetermined thresholds 124. Optionally, time delay estimation techniques developed for sonar and radar applications are used to improve the robustness of the $\Delta\tau$ determination. However, the accuracy of these methods depends on the sampling period. For example, a sampling rate of 10 MHz has a sampling period of 0.1 μs. For long distances and, therefore, large time scale applications such as radar or sonar the sampling period is not a significant factor. However, in intracranial applications the distance traveled by an ultrasonic pulse signal is relatively short—twice the diameter of the brain—and, therefore, the sampling error is significant unless an extremely high sampling frequency is used, making a system implementation prohibitively costly for most medical applications. Equation (3) is a simplistic expression deriving $\Delta\tau$ for two—the $i^{th}$ and $(i+1)^{th}$—ultrasonic pulses:

$$\Delta\tau = t_{i+1} - t_i \tag{3}$$

Error=$\pm t_{sp}$ (sampling period)

Figure 3:
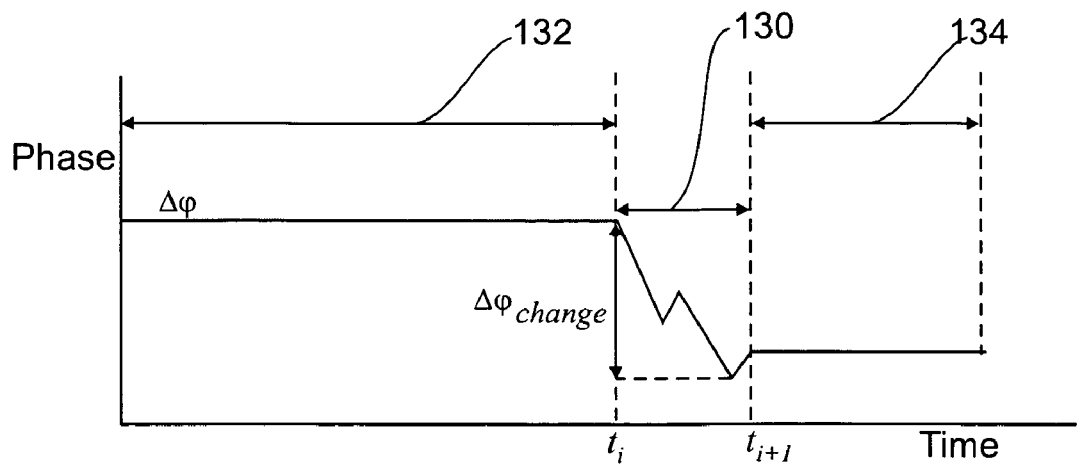
FIG. 3 is a simplified diagram illustrating a response signal using a method for non-invasive monitoring of brain density variations according to the invention.

In the method and apparatus for non-invasive monitoring of brain density variations according to the invention the object is to monitor variations in the time delay $\Delta\tau$ with respect to a first observation. Determination of $\Delta\tau$ does not provide sufficient sensitivity for detecting minor density variations in intracranial applications, for the reasons discussed above. Therefore, in the method and apparatus for non-invasive monitoring of brain density variations according to the invention a relative phase difference $\Delta\phi$ between phases of transmitted and reflected pulses is determined. The phase difference $\Delta\phi$ is given by:

$$\Delta\phi = \phi(r) - \phi(t) \tag{4}$$

where $\phi(r)$ is the phase of the reflected pulse and $\phi(t)$ is the phase of the transmitted pulse. Determining the phase difference $\Delta\phi$ does not require a high sampling frequency and, therefore, provides a substantially higher accuracy than the determination of the time delay $\Delta\tau$. Therefore, a minor change in density $\rho$ appears as a change in $\Delta\phi$, as shown in FIG. 3 illustrating a phase change due to a density changing event 130 in a brain between normal state of constant phase 132 and a new equilibrium of constant phase 134. The phase variation $\Delta\phi_{change}$ 130 is directly related to a density variation $\Delta\rho$ in the brain tissue. The phase variation $\Delta\phi_{change}$ is related to a variation in traveling time by the following equation:

$$\Delta\tau_{change} = \frac{\Delta\varphi_{change}}{2\pi f} \quad (5)$$

Assuming the dimension (D) of the skull remaining constant, a variation in traveling time is only caused by an intracranial change in sound velocity c:

$$\Delta\tau_{change} = \left(\frac{2D}{c_{i+1}}\right)_{t_{i+1}} - \left(\frac{2D}{c_i}\right)_{t_i} \quad (6)$$

A change in density $\Delta\rho$ is responsible for the change in the sound velocity c since K(f) in equation (1) is constant for a specific frequency and medium. $\Delta\rho$ and $\Delta\phi_{change}$ are included in equation (6) as follows:

$$\Delta\tau_{change} = \frac{2D}{\sqrt{K/\rho+\Delta\rho}} - \frac{2D}{\sqrt{K/\rho}} \quad (7)$$

$$\Delta\tau_{change} = \frac{2D}{\sqrt{K}}\left[\sqrt{\rho+\Delta\rho} - \sqrt{\rho}\right] \quad (8)$$

$$\Delta\varphi_{change} = 2\pi f \frac{2D}{\sqrt{K}}\left[\sqrt{\rho+\Delta\rho} - \sqrt{\rho}\right] \quad (9)$$

Figure 4:
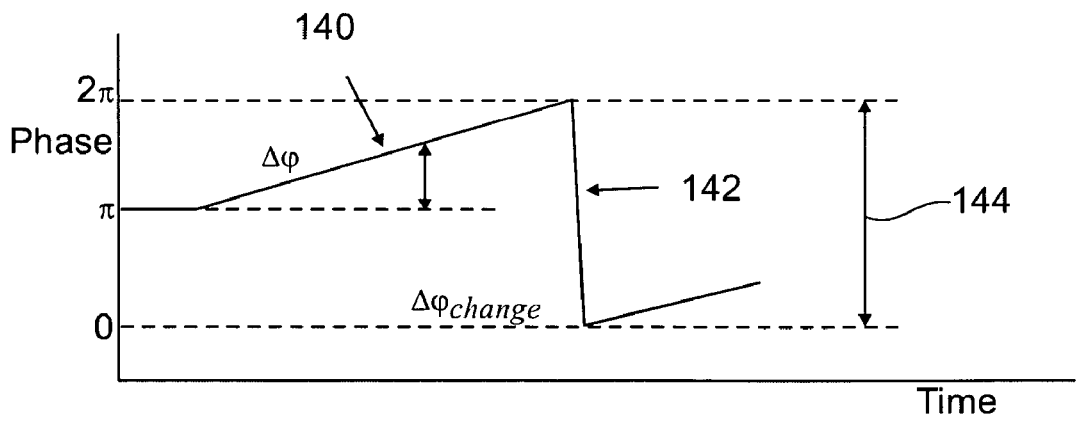
FIG. 4 is a simplified diagram illustrating a range of operation of the method for non-invasive monitoring of brain density variations according to the invention.

Although the determination of the variation in phase—$\Delta\phi_{change}$ in Equation (9)—provides a substantially improved sensitivity compared to the determination of a variation in time delay $\Delta\tau$, the determination of the variation in phase is not always accurate because of phase wrapping. If a phase change is greater than plus or minus half a wavelength, equation (9) is not sufficient for monitoring a density variation. The variation in phase $\Delta\phi_{change}$ is only reliable for a small range of $\Delta\tau_{change}$ in which the phase does not wrap, determined by the period of the acoustic signal. As an example, we consider a narrowband ultrasonic pulse with a frequency of 1.5 MHz and thus a period of 0.67 µs traveling through a medium with a phase velocity of 1500 m/s. Using a brain diameter (D) of 10 cm and assuming $\Delta\phi$ being initially half a wavelength, the percentage density change detected accurately before phase wrapping is calculated using equation (8) to be ±0.5%. This range does not sufficiently cover larger changes in brain density. In fact, the initial $\Delta\phi$ being half a wavelength is a best-case scenario. If the initial $\Delta\phi$ is 350°, for example, only an increase of 10° is detected accurately. FIG. 4 illustrates the determination of the variation in phase using one transmitted frequency comprising a gradual rise in phase due to density change 140, a wavelength shift due to wrapping 142 within a range of operation 144.

Hence, in order to accurately determine $\Delta\tau_{change}$ from $\Delta\phi_{change}$, the number of wavelength shifts—$N_{change}$—is accounted for. Equations (5) and (9) have been modified to account for the number of wavelength shifts forming equations (10) and (11):

$$\Delta\tau_{change} = \frac{2\pi N_{change} + \Delta\varphi_{change}}{2\pi f} \quad (10)$$

-continued $$\Delta\varphi_{change} = 2\pi f \frac{2D}{\sqrt{K}}\left[\sqrt{\rho+\Delta\rho} - \sqrt{\rho}\right] - 2\pi N_{change} \quad (11)$$

$N_{change}$ is determined by using two transmit frequencies that are related as follows:

$$f_2 = \frac{n}{m} f_1, \quad m, n \in N, \quad (12)$$

and $$\Delta\varphi_{change}(f_1) = 2\pi f_1 \frac{2D}{\sqrt{K(f_1)}}\left[\sqrt{\rho+\Delta\rho} - \sqrt{\rho}\right] - 2\pi N_{change} \quad (13)$$

$$\Delta\varphi_{change}(f_2) = 2\pi f_2 \frac{2D}{\sqrt{K(f_2)}}\left[\sqrt{\rho+\Delta\rho} - \sqrt{\rho}\right] - 2\pi N_{change} \quad (14)$$

The beating between the two transmitted frequencies is used to extend the operating range to the beat period $T_{beat}$ and to accurately calculate $N_{change}$. The beat period between the two transmitted frequencies is defined as follows:

$$T_{beat} = \frac{1}{|f_2 - f_1|} \quad (15)$$

Equations 12 and 15 are then combined to form the following relationship for given n>m:

$$T_{beat} = \frac{m}{n-m} T_1 \quad (16)$$

or $$T_{beat} = \frac{n}{n-m} T_2,$$

where $$T_{1,2} = \frac{1}{f_{1,2}}.$$

Figure 5:
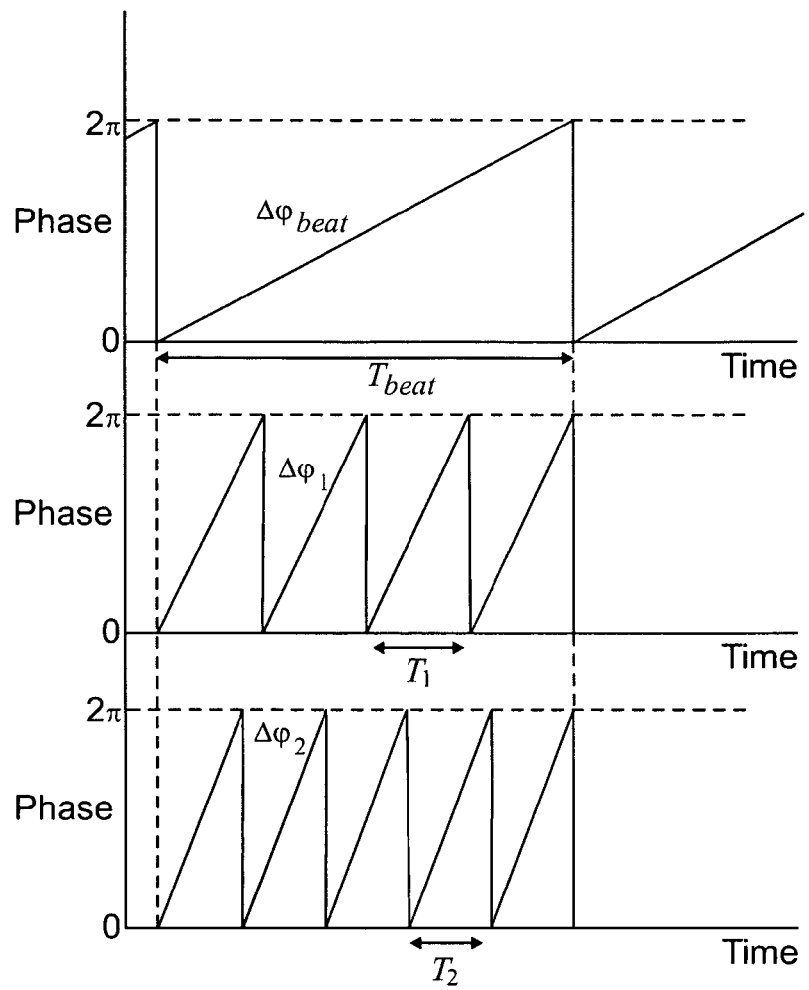
FIG. 5 is a simplified diagram illustrating phase of beat frequency and individual frequencies of a pulse signal in the method for non-invasive monitoring of brain density variations according to the invention.

The following example demonstrates the process of using the phase of the beat frequency to calculate $N_{change}$. In this example, two transmit frequencies are related as follows: $f_2 = \frac{5}{4} f_1$. FIG. 5 provides a schematic representation of the phases for $f_1$, $f_2$ and $f_{beat}$. The phase of the beat frequency is determined using the following relationship:

$$\Delta\phi_{beat} = \Delta\phi_2 - \Delta\phi_1 \bmod 2\pi \quad (17)$$

Figure 6:
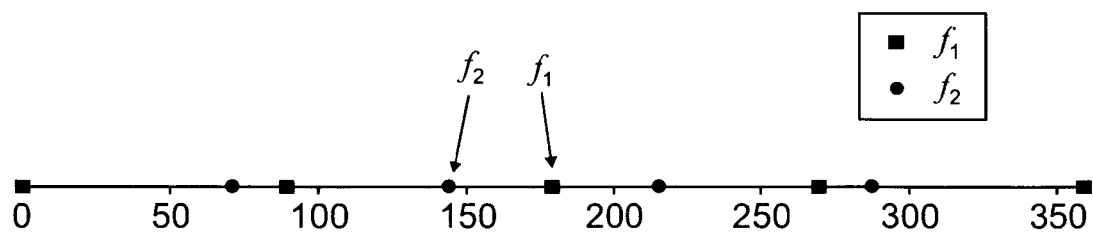
FIG. 6 is a simplified diagram illustrating beat frequency values for wavelength shifts of a response signal using the method for non-invasive monitoring of brain density variations according to the invention.

FIG. 5 illustrates that during one beat period $T_{beat}$, the transmit frequency $f_1$ shifts from $2\pi$ to 0 four times, and the transmit frequency $f_2$ shifts five times. In other words, for $f_1$ there are four wavelength shifts—$N_{change}=4$—and for $f_2$ there are five wavelength shifts—$N_{change}=5$. These changes occur at unique points during the beat period $T_{beat}$, therefore, it is possible to count the wavelength shifts $N_{change}$ using, for example, a look-up table. Furthermore, the range of operation is extended to the beat period $T_{beat}$ since the wavelength shifts in that range are known. The values of the beat frequency phase at which wavelength shifts occur for either transmit frequency are shown in FIG. 6.

Figure 7:
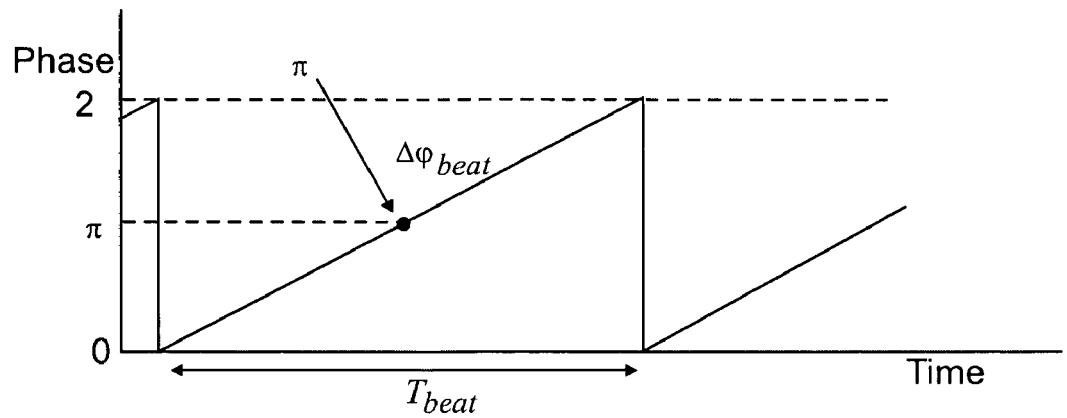
FIG. 7 is a simplified diagram illustrating an initial beat frequency phase of a pulse signal in the method for non-invasive monitoring of brain density variations according to the invention.

Although a long beat period has the advantage of creating a wider range of operation, more wavelength shifts of $f_1$ and $f_2$ are resolved over the same range of $2\pi$. If the spacing between wavelength shifts becomes smaller than the accuracy of the phase measurements, the measurement is no longer reliable. Furthermore, to fully exploit the entire beat period $T_{beat}$ the initial beat frequency phase $\Delta\phi_{beat}$ is preferably chosen to be close to $\pi$ or 180°. As illustrated in FIG. 7, the $f_1$ and $f_2$ wavelength shifts have greater angular difference when the initial beat frequency phase $\Delta\phi_{beat}$ is near the center of the $2\pi$ range. The initial beat frequency phase $\Delta\phi_{beat}$ is dependent on the initial phases of the individual frequencies, which are in turn dependent on the frequencies of the acoustic signals used, the density of the brain and its dimensions. If the frequencies $f_1$ and $f_2$ are fixed, the initial phase is located anywhere in the range of $2\pi$, but the use of a wide operating range improves the situation. Alternatively, the frequencies $f_1$ and $f_2$ are variable and are then adjusted to have the initial beat frequency phase $\Delta\phi_{beat}$ near the center of the $2\pi$ range, while still meeting the criteria of equation (12).

Fixed or variable transmit frequencies are generated using an ultrasonic pulse generators such as a Direct Digital Synthesizer (DDS). A readily available DDS is able to generate an output sine wave of up to 150 MHz, which is digitally tunable at a rate of 100 million new frequencies per second. Using the DDS, the non-invasive technique for monitoring brain density variations according to the invention is not limited to only two transmit frequencies but utilizes a plurality of transmit frequencies $f_n$, n=1, 2 . . . N. Therefore, the technique comprises more than one beat period $T_{beat}$ as long as all the transmitted frequencies meet the criteria of equation (18), which is an extension of equation (12):

$$f_1 = \frac{n_2}{m_2} f_2 = \frac{n_3}{m_3} f_3 = \ldots, \text{ where } n_x, m_x \in N \quad (18)$$

Figure 8:
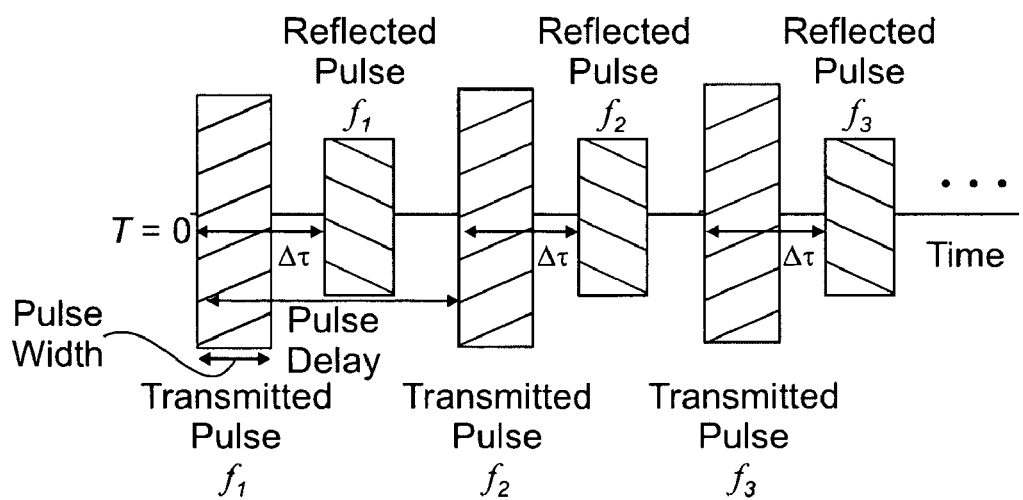
FIG. 8 is a simplified diagram illustrating transmit and receive pulses of the method for non-invasive monitoring of brain density variations according to the invention.

Having different beat periods permits different operating ranges and allows for multiple determination of $N_{change}$ and $\Delta\phi_{change}$, thereby improving the precision of the technique and enabling an accurate representation of the dispersive properties of the brain—$K(f)=\gamma B_T(f)$—as expressed in equation (1). Since the phase of the beat frequency is only determined by the phases of the individual transmit frequencies it is possible to transmit the ultrasonic pulses separately, as shown in FIG. 8.

As discussed above, the beat period is an important consideration in frequency selection, but other parameters limit the choice of the transmission frequencies. For monitoring brain density variations the acoustic signal has to travel through the skull and the brain. There is a relatively low attenuation window for ultrasonic waves to penetrate the skull—2.5 MHz and below. 0.5 MHz to 2.5 MHz has been found as a viable range for the transmission frequencies. The large transmission window from 0.5 MHz to 2.5 MHz, permitting a large number of transmission frequencies, introduces a new phenomenon. The velocity of sound in water is dispersive and the brain—being composed of approximately 80% water—is subject to the same effect, as shown in equation (1). Early testing indicated a significant difference in the sensitivity of different transmit frequencies to various pathological conditions—possibly related to the dispersive nature of the brain tissue. Through clinical trials it has been found that it is possible to establish a correlation between various pathological conditions such as stress and pain, hemorrhage, edema, etc. and the most responsive frequencies. Therefore, the use of multi-frequency transmit signals in the non-invasive technique for monitoring brain density variations according to the invention enables non-invasive assessment of brain trauma or other pathological conditions of a patient's brain providing a powerful tool for intracranial diagnostics.

Another criterion for selecting the transmit frequencies is the sampling rate. An Analog-to-Digital Converter (ADC) converts the ultrasonic pulses into digital form to enable a processor to calculate the relevant phase information from the transmitted and the received ultrasonic pulses. Because only the phase information is needed it is possible to choose the sampling frequency $f_{samp}$ of the ADC independent of the Nyquist frequency, resulting in possible under-sampling. To avoid under-sampling the sampling frequency satisfies the condition that complete periods of the respective signals are sampled as given in equation (19):

$$f_{samp} = \frac{n_1}{m_1} f_1 = \frac{n_2}{m_2} f_2 = \frac{n_3}{m_3} f_3 = \ldots, \text{ where } n_x, m_x \in N \quad (19)$$

The transmit frequencies are variable, but a fixed sampling frequency $f_{samp}$ of the ADC limits the number of frequencies satisfying equation (19). An ADC that uses a variable sampling frequency allows unlimited choice of frequencies but adds considerably to the complexity of the hardware implementation of the technique.

Figure 9:
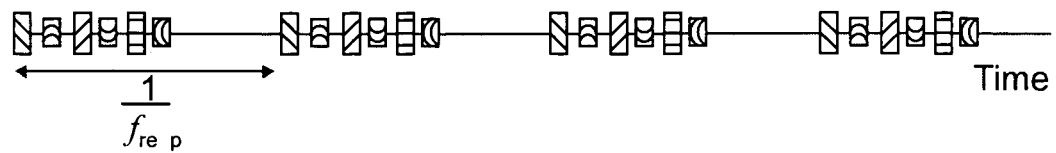
FIG. 9 is a simplified flow diagram illustrating a repetition of transmit and receive pulses of the method for non-invasive monitoring of brain density variations according to the invention.
Figure 10:
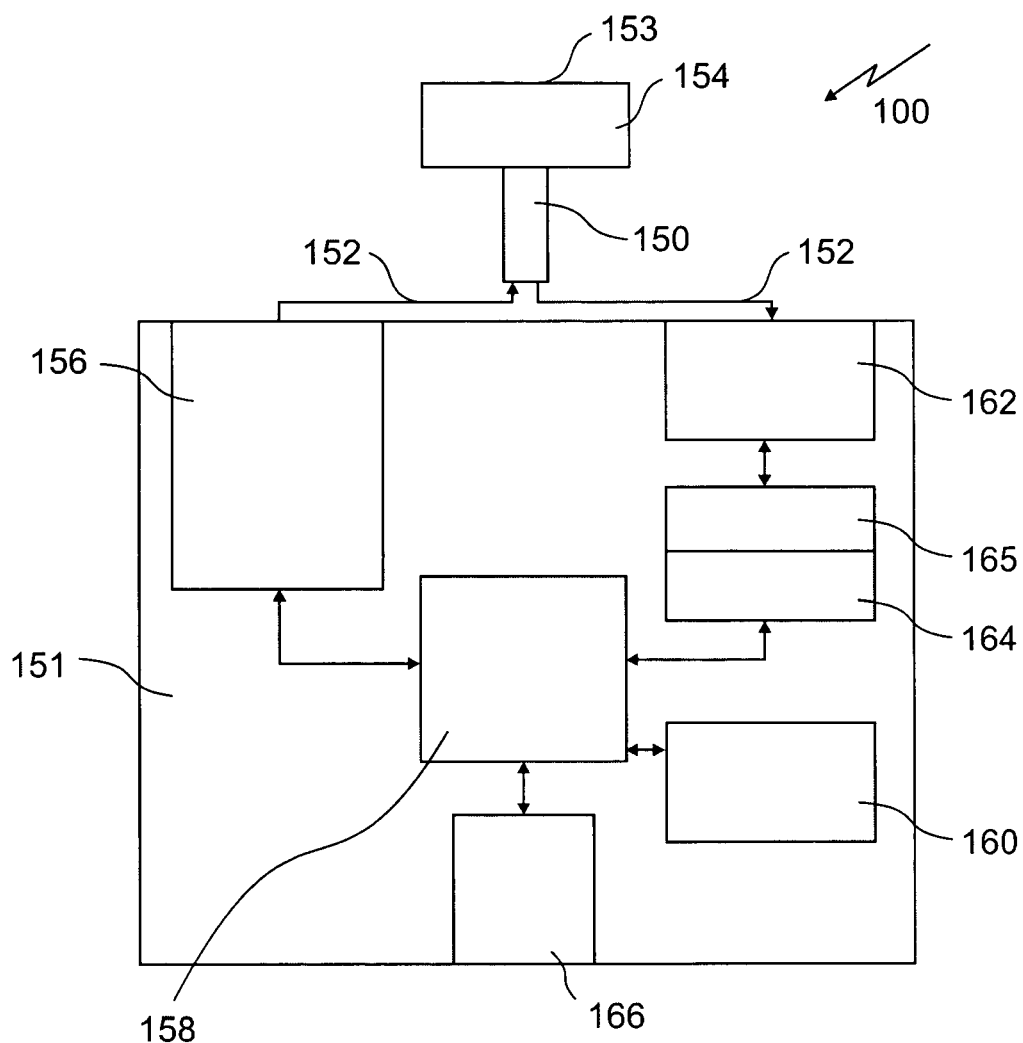
FIG. 10 is a simplified block diagram illustrating an apparatus for non-invasive monitoring of brain density variations according to the invention.

The ultrasonic wave pulses are generated, for example, on a DDS frequency generation board. Parameters such as the number of pulses, pulse frequency, width, delay, and repetition rate $f_{rep}$ are controlled from the board. In order to continuously monitor the phase relationship $\Delta\phi$ with respect to the first observation for tracking brain density variations the pulses are repeatedly transmitted. A high repetition rate enables near real-time observations, but also requires large storage space and high execution speed. The limitation on the pulse width to avoid overlap between the transmitted and the reflected pulse is given by:

$$t_i < \frac{2D}{c} \quad (20)$$

where $$t_i = \frac{1}{f_{rep}}$$

is the width of a packet of ultrasonic pulses, as shown in FIG. 9. The pulse delay is also chosen such that overlap between reflected and transmitted pulses of different frequencies is avoided.

Figure 11:
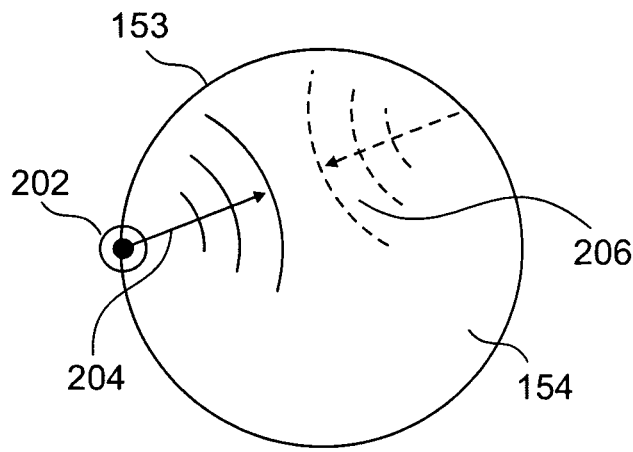
FIG. 11 is a simplified diagram illustrating sensing of reflected ultrasonic pulses using 3D beam steering in the method for non-invasive monitoring of brain density variations according to the invention.

Referring to FIG. 11, a preferred embodiment of an apparatus for non-invasive monitoring of brain density variations 100 according to the invention is shown. The apparatus 100 comprises a transducer 150 for coupling transmit ultrasound pulses into a medium of interest 154 such as a human brain confined within closed solid boundaries 153 such as a skull, and for sensing the transmit ultrasound pulses reflected from the solid boundaries 153. Alternatively, a transmitter and a sensor are disposed separately enabling, for example, disposing of the transmitter and the sensor on opposite locations of the skull for sensing ultrasonic pulses without being reflected. The transducer 150 is connected to a processing unit 151 such as a portable computer via cable 152 for transmitting the transmit ultrasound pulses from a DDS frequency generation board 156 and for transmitting sensed reflected ultrasound pulses to filtering and amplification unit 162. The DDS frequency generation board 156 generates the transmit ultrasound pulses in dependence upon at least a control signal received from processor 158. The received ultrasound signals are filtered and amplified in the filtering and amplification unit 162 and then converted into corresponding digital signal data using ADC unit 164. Optionally, the ADC unit 164 comprises buffer memory 165 in the form of RAM for storing the digitized data prior processing. The ADC unit 164 is in communication with the processor 158 for providing the digital signal data as well as for receiving at least a control signal. Optionally, the ADC unit 164 is operable using a variable sampling frequency predetermined by the processor 158. The processor controls the DDS frequency generation board 156 and the ADC unit 164 and processes the digital signal data. Preferably, a graphical user interface 166 is used to receive instructions from a user such as a medical practitioner and to display the processed signal data. Further preferably, the processing unit comprises non-volatile memory 160 in communication with the processor for storing the digital signal data as well as for storing data indicative of signal patterns obtained in prior clinical trials for comparing the digital signal data therewith.

The coupling between the transmit-receive transducer and the medium of interest is critical when a single transducer is employed because the reception of a useful reflected signal requires that opposing walls in the transmit—reflect direction are parallel. Because of this restriction there are a limited number of locations for placing the transducer on the skull, i.e. over the temporal bone, in order to achieve a good transducer-medium coupling interface that allows good reception of the reflected signals. To overcome this restriction the apparatus for non-invasive monitoring of brain density variations 100 according to the invention, preferably, comprises a circular transducer array that includes a plurality of detectors such as a circular array probe 202, as shown in FIG. 11. The circular array probe enables generating digital 3-dimensional steering beams using beamformers, as is known to those of skill in the art. Implementing 3D steering beams overcomes the restriction that opposing walls facing the transducer have to be parallel. The 3D beam steering is able to detect the reflected 206 as shown in FIG. 11. Furthermore, the 3D beam steering reduces sensitivity of the apparatus for non-invasive monitoring of brain density variations 100 according to the invention to motion effects of the skull present during diagnostic procedures, especially during emergency and rescue operations.

The non-invasive technique for monitoring brain density variations according to the invention depends on an accurate determination of the phase properties of each transmitted and received ultrasound pulse. The resolution of the ADC directly influences the accuracy of the phase determination. A 12-bit ADC provides sufficient resolution for ensuring a phase evaluation error for each measurement of less than 1°. The width of the ultrasonic pulses and the sampling frequency determine the number of data points used to calculate the phase of the pulse, with the width being limited by the condition of equation (20). Equation (20) yields a maximum pulse width of approximately 130 μs for a velocity of sound of 1540 m/s in brain tissue and an average skull diameter of 10 cm. It is possible to use pulses of significantly shorter pulse width allowing for variations in the skull diameter. Two different methods to determine the phase of the transmitted and reflected pulses have been developed and incorporated in the non-invasive technique for monitoring brain density variations according to the invention.

The first step in both methods is finding the position of the transmitted and the reflected pulses in order to determine the phase. The positions of the transmit pulses are predetermined because pulse width and pulse delay are controlled by the DDS frequency generation board. The positions of the reflected pulses vary depending on the physical properties—the velocity of sound and the density—and the dimensions of the object. A process has been implemented for finding the edges of the reflected pulses using the Hilbert transform for calculating the envelope of the signal, therefore, enabling locating the position of all the pulses.

Figure 12:
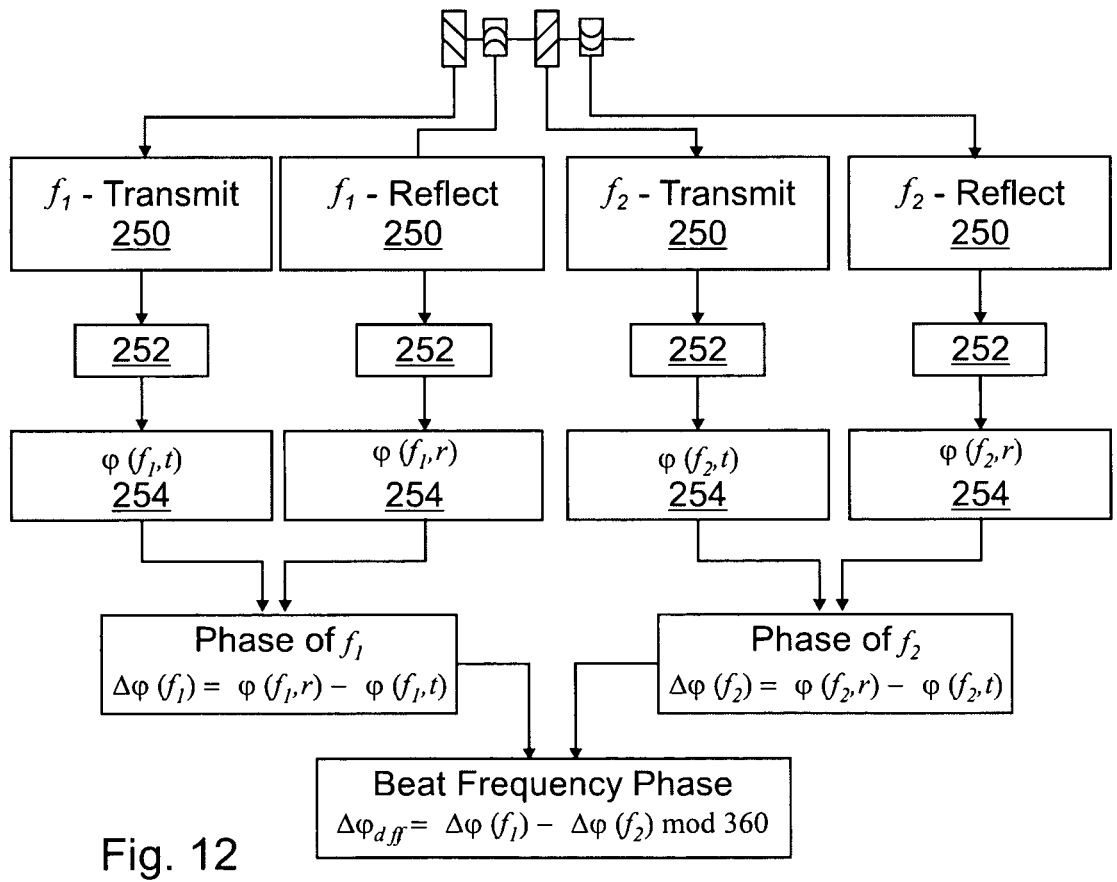
FIG. 12 is a simplified flow diagram illustrating phase determination in the method for non-invasive monitoring of brain density variations according to the invention.

In the first method—FFT method—shown in FIG. 12, sample points from the center of each pulse are selected while sampling complete periods of the selected central points—box 250. For example, if $$f_{samp} = \frac{7}{3}$$

$f_1$, then 7 sampling points represent 3 complete periods of $f_1$. Some multiple of 7 sample points are then zero padded—box 250. Next, a hamming window and FFT is applied on the data—box 252. The phase of each pulse is then determined using the frequency bin closest to the transmitting frequency, $f_1$, $f_2$, $f_3$, etc.—box 254.

An alternative method uses an analytic Fourier transform process. The analytic Fourier transform process determines a DFT coefficient at the transmitted frequencies, which are then used to determine the phase of the wave. It also uses samples of complete periods to determine the phase. This method reduces computational complexity without sacrificing accuracy compared to the FFT method, because only one coefficient is calculated. Additionally, a specific frequency is chosen instead of finding the closest bin.

Figure 13:
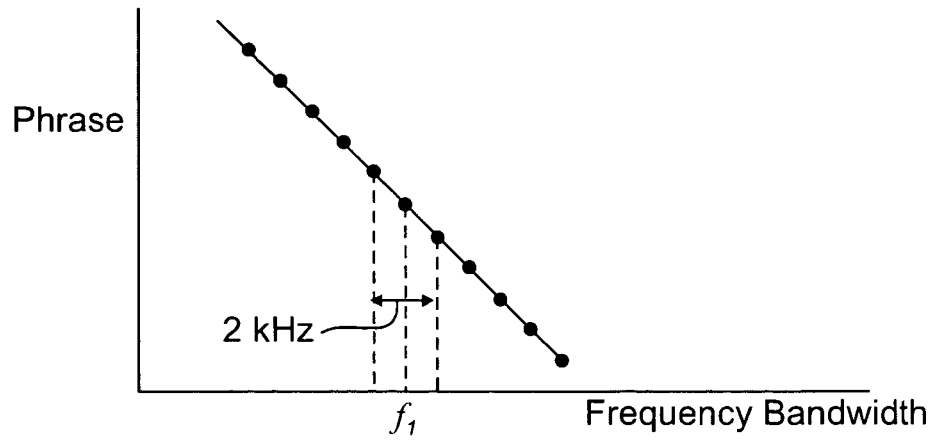
FIG. 13 is a simplified diagram illustrating a linear relationship between phase and frequency in the method for non-invasive monitoring of brain density variations according to the invention.
Figure 14:
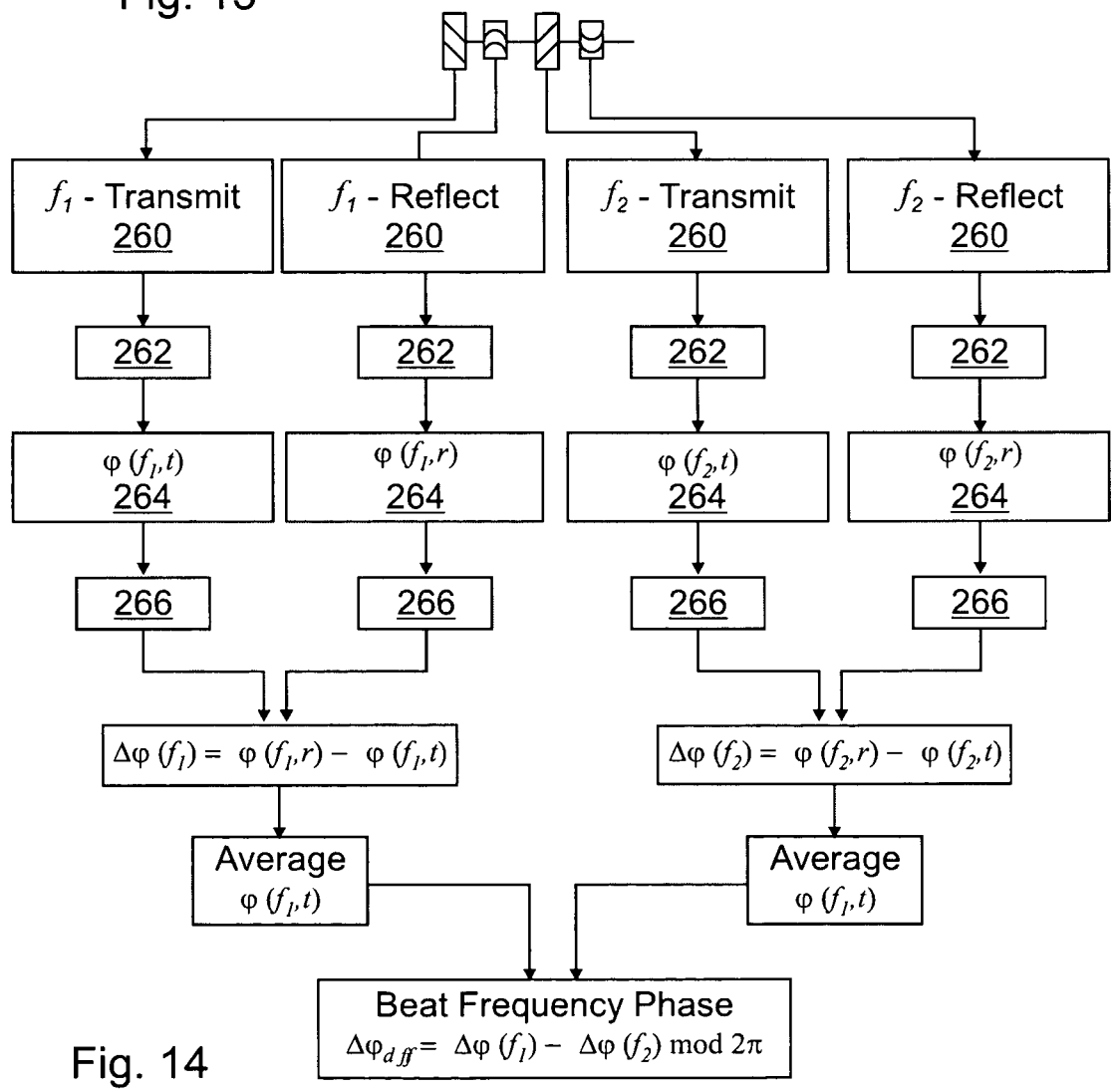
FIG. 14 is a simplified flow diagram illustrating phase determination in the method for non-invasive monitoring of brain density variations according to the invention.

Optionally, additional phase calculations are made around the center frequency to increase robustness. A wider bandwidth allows numerous phase determinations. For example, in the process eleven phase determinations spaced 2 kHz apart around the center bandwidth frequency of the transmitted pulse are used, as shown in FIG. 13. Alternatively, the extra phases are determined by applying the FFT method and using the frequency bin around the center frequency. The relationship between the eleven phase determinations and the relevant frequencies is linear, as shown in FIG. 13. The linearity is useful for testing whether noise or interference has influenced the measurements. For example, if one or more of the data points deviate from the expected linear relationship, the erroneous point is removed, increasing the robustness of the technique. The remaining data points are then averaged to determine the phase. Additionally, the accuracy of the measurement is determined by correlating the data points with the expected linear relationship. A simplified flow diagram of the second method is shown in FIG. 14. For each transmitted and reflected pulse center data points are selected—box 260. At each transmitting frequency and 10 surrounding points analytic Fourier transformation is applied—box 262—and the phase of the eleven points is then determined—box 264. This step is followed by testing the linearity of the eleven phase points and removing erroneous points—box 266. Further steps are determining the phase differences, averaging the phase differences for the various points and determining the beat frequency phase.

Figure 15:
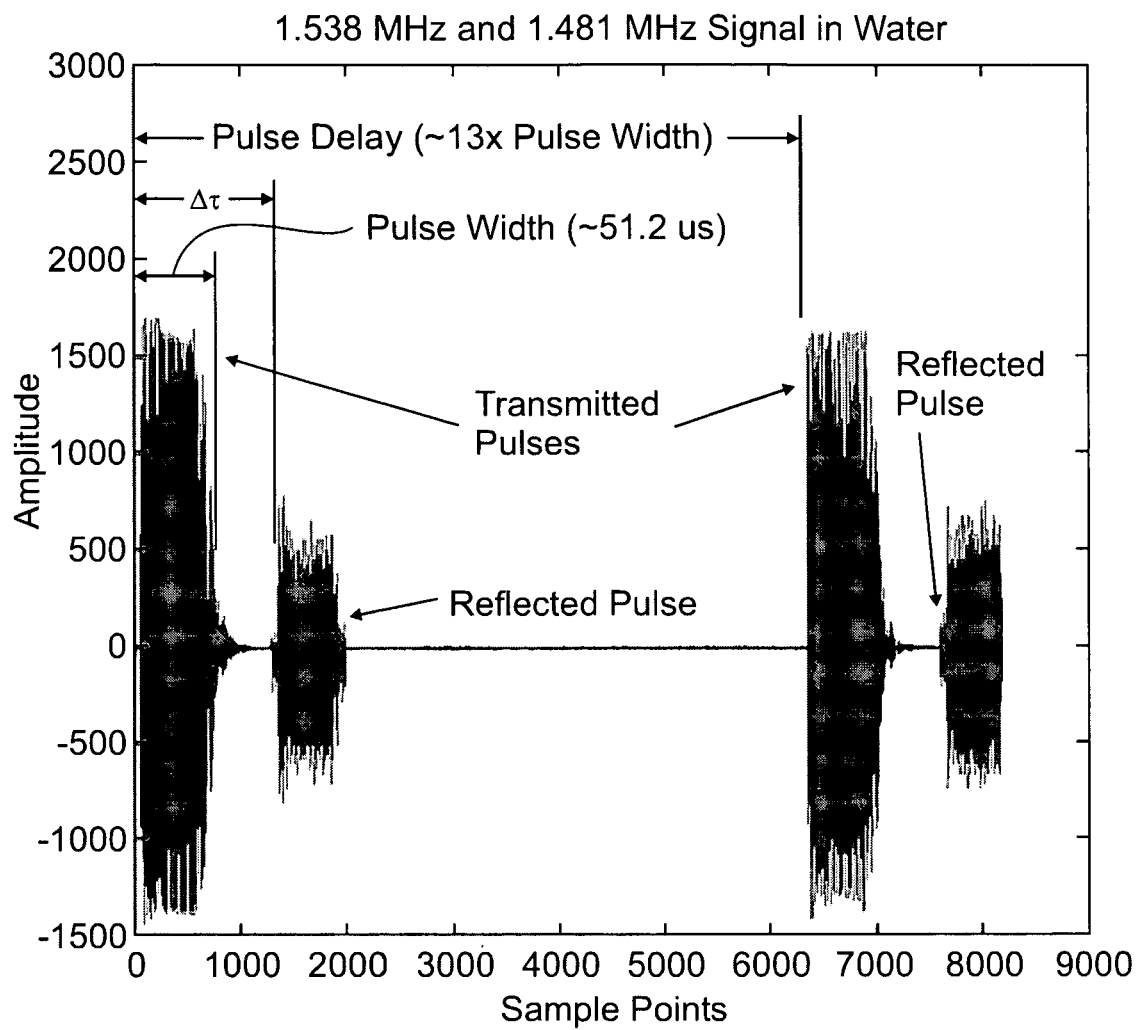
FIGS. 15 and 16 are diagrams illustrating various signal responses of a first experiment using the method for non-invasive monitoring of brain density variations according to the invention; and, FIGS. 17 to 20 are diagrams illustrating various signal responses of a second experiment using the method for non-invasive monitoring of brain density variations according to the invention.
Figure 16:
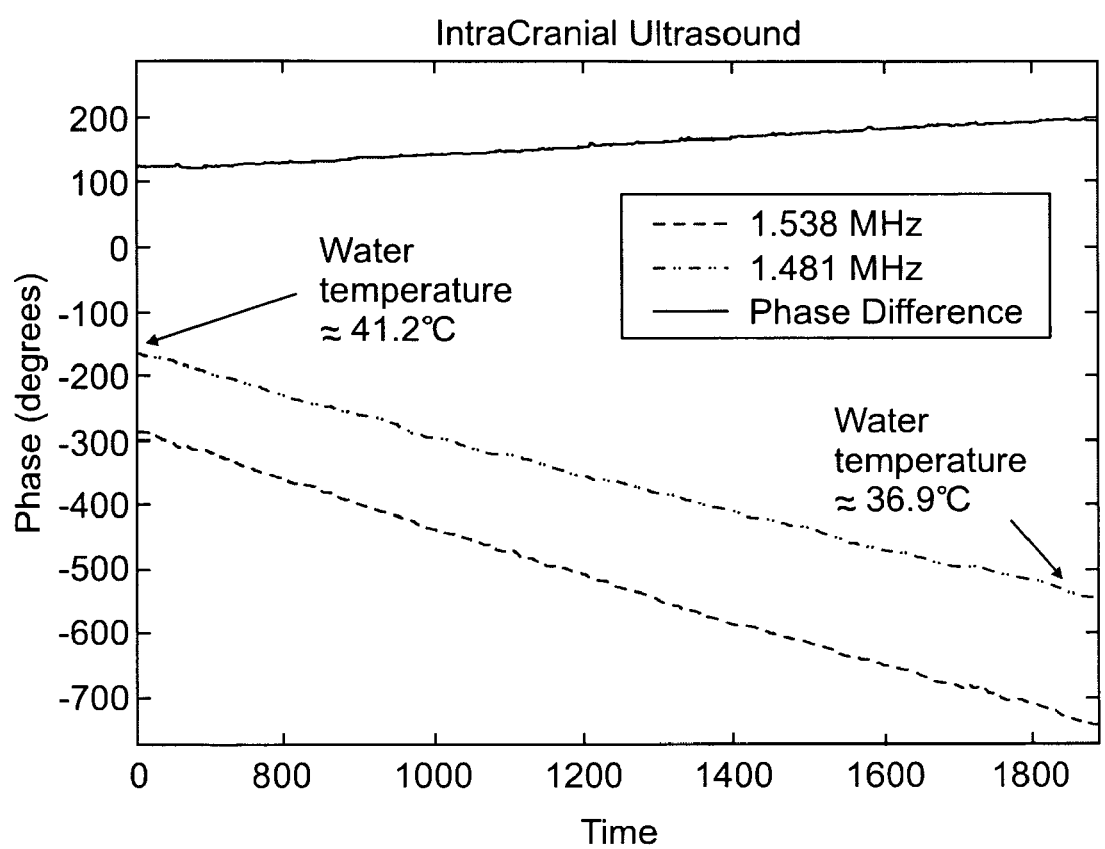

The non-invasive technique for monitoring brain density variations according to the invention has been tested using two different experiments. In the first experiment water inside a rectangular Plexiglas container approximately 10 cm wide was used. The transducer was placed on one side of the container and the coupling between the container and the transducer was improved using standard ultrasonic probe gel. FIG. 15 shows the signal response from this experimental setup. To demonstrate the technique's sensitivity in determining $\Delta\phi$ corresponding to changes in density, the water was slowly cooled, increasing the density of water. FIG. 16 shows results of $\Delta\phi$ corresponding to a linear decrease in water temperature.

Figure 17:
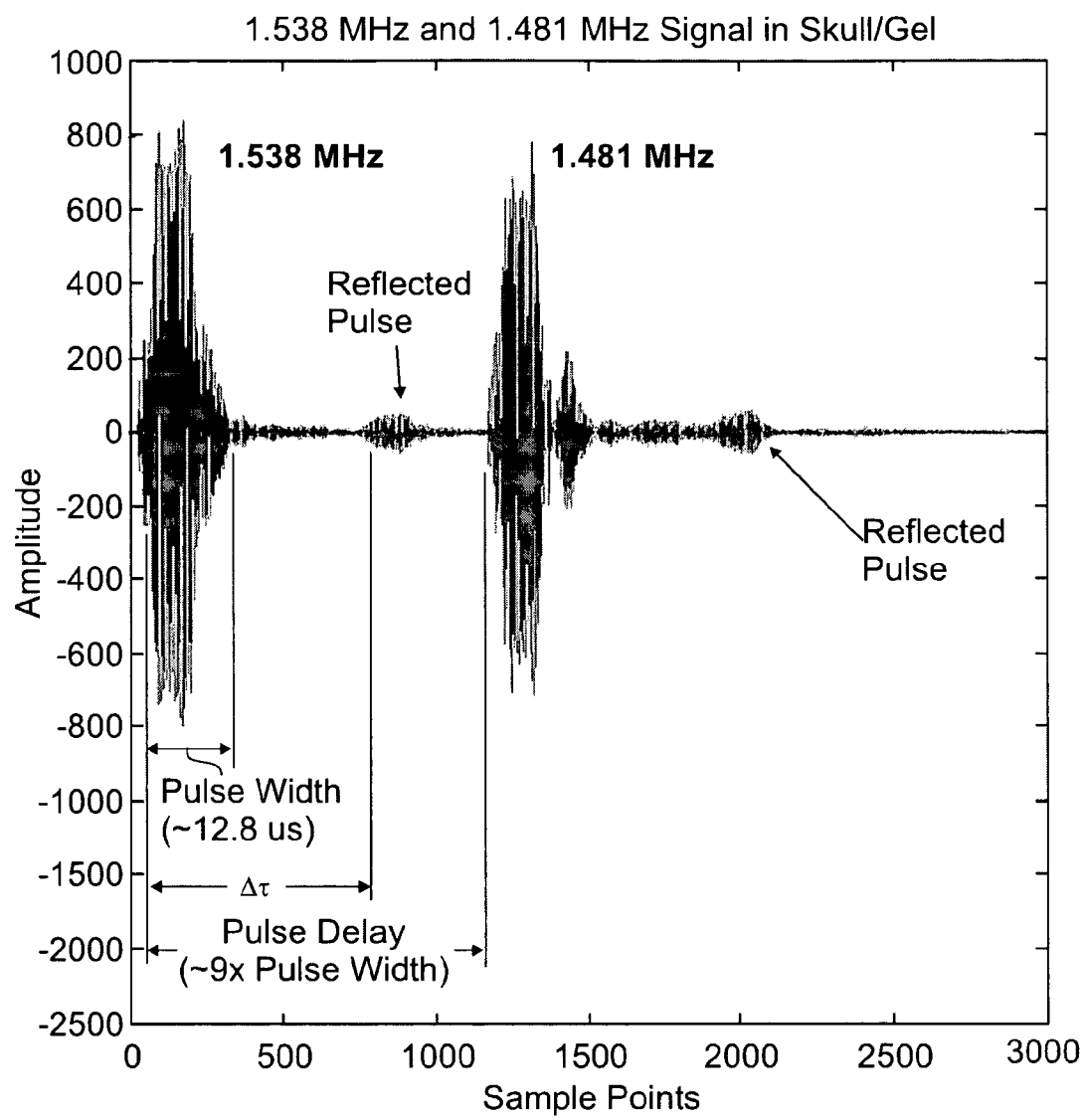
Figure 18:
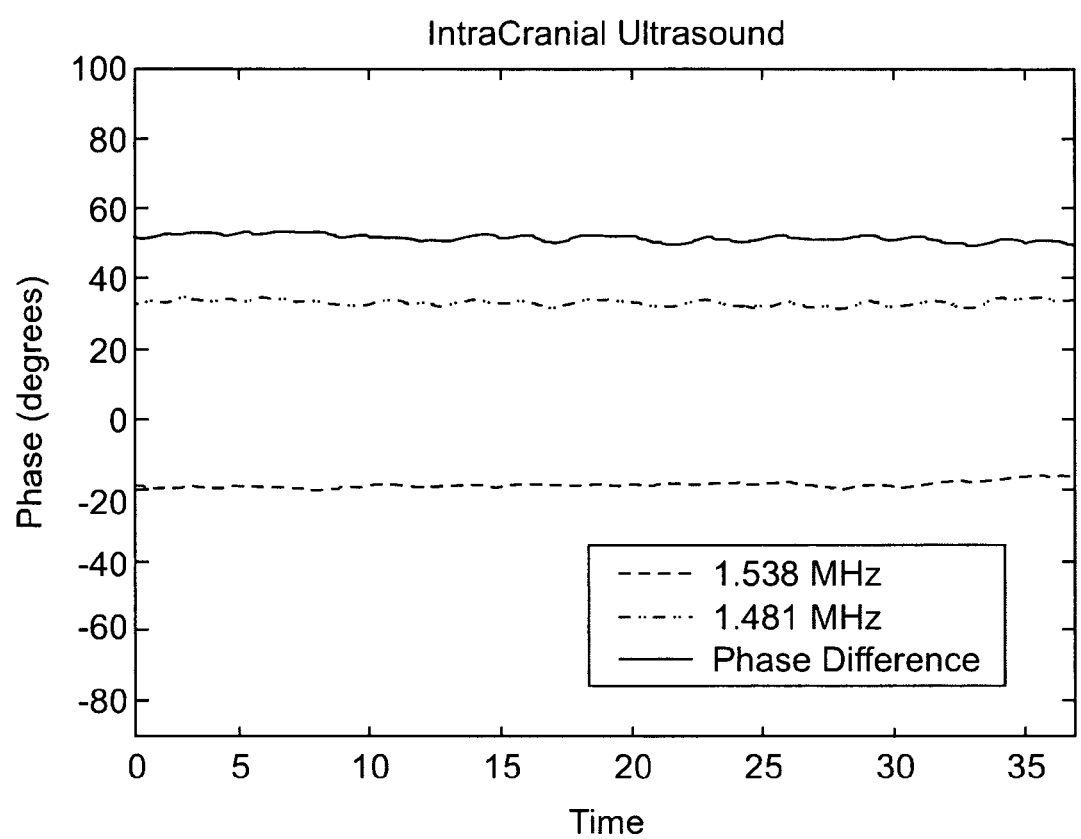

A more realistic experiment was performed using a primate skull. The skull was filled with standard ultrasonic probe gel of constant density. The same gel was also used to couple the transducer and the temporal bone of the skull. Although the reflected signal from the interior walls of the skull was significantly attenuated and the Signal-to-Noise-Ratio (SNR) was significantly lower compared to the signal in FIG. 15, the reflected pulse had a sufficiently high SNR to provide good results for $\Delta\phi$ as is clearly shown in FIG. 17. In the primate skull experiment, with no density variations present, which is the case for a healthy human brain, $\Delta\phi$ is expected to be constant. FIG. 18 shows the result—constant $\Delta\phi$—for a period of constant density.

Figure 19:
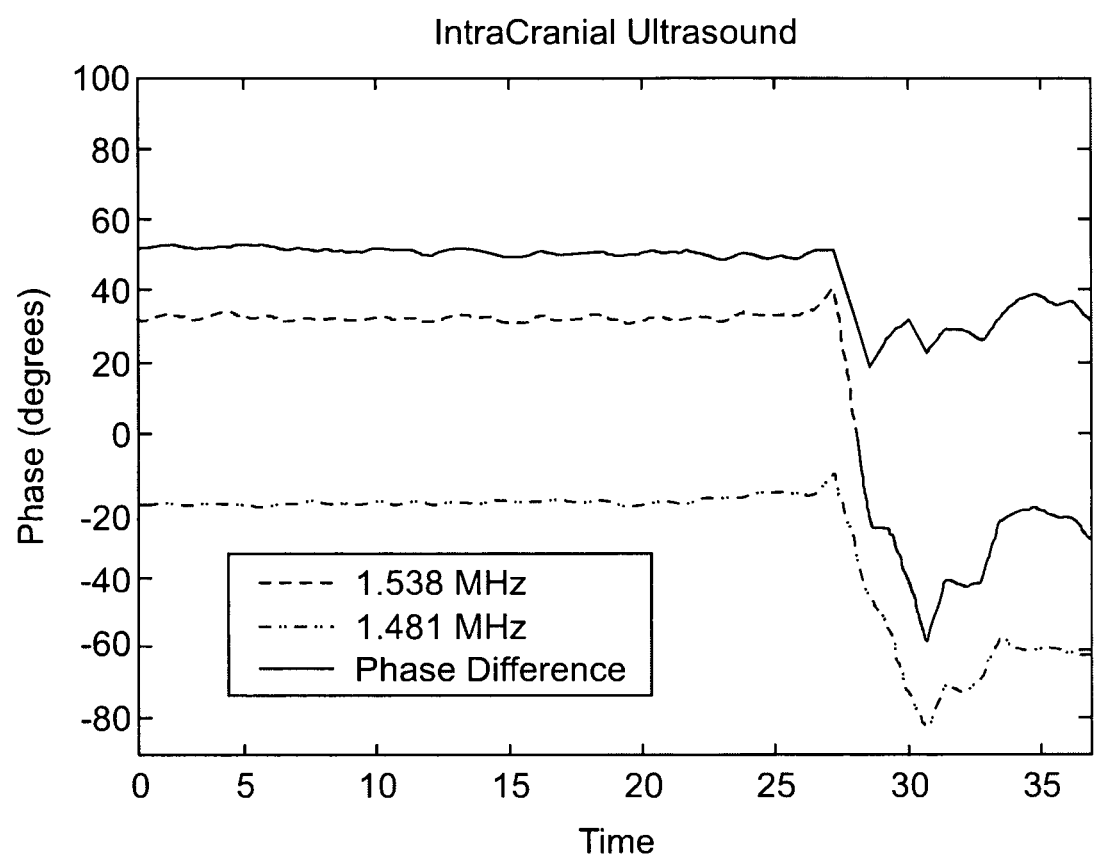
Figure 20:
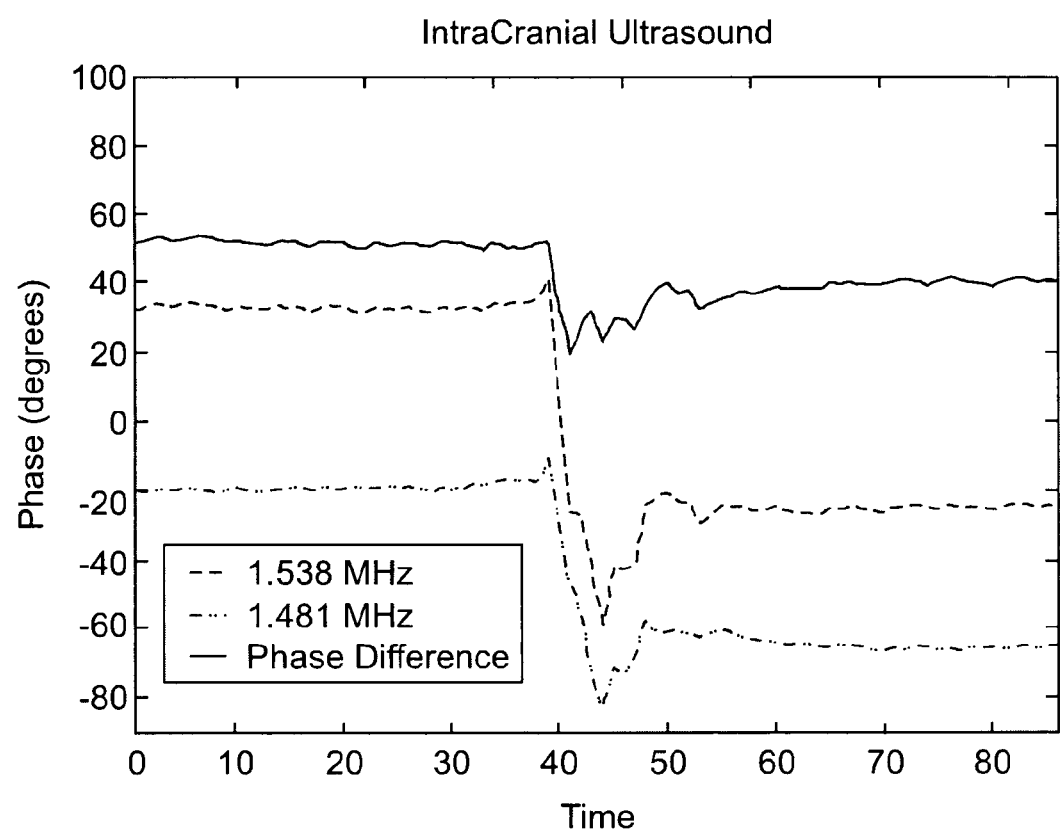

To simulate a change in brain density—comparable to a brain hemorrhage—the intracranial cavity of the primate skull is filled with ultrasonic gel and then disturbed by injecting 2 ml of water into the skull through the eye socket. The density variation caused by the injection causes variations in $\Delta\phi$, as shown in FIG. 19. The results provide a qualitative assessment of the techniques dynamic response for the case of water flow through a gel-filled skull similar to a real-time response to a brain hemorrhage. Following the injection of water into the primate skull, the intracranial gel-water mixture reaches a new state of density equilibrium. The density of the new mixture is slightly different than that of the original gel because some of the gel has been replaced with water. FIG. 20 shows results of $\Delta\phi$ corresponding to the new state of density equilibrium for the primate skull, which is a follow-up of the results presented in FIG. 19.

The method and apparatus for non-invasive monitoring of brain density variations according to the invention is highly beneficial in numerous applications. Firstly, in clinical settings it enables monitoring of a pathological condition of a patient's brain with a same accuracy as invasive techniques but obviating surgery and, thus, risk of infection. Therefore, it allows accurately monitoring brain density variations in substantially more cases such as patients in critical condition and or in situations where the risk of infection outweighs the benefit of monitoring brain density variations. Furthermore, the apparatus 100 is implemented in a highly compact fashion such as a portable computer with a transducer connected thereto and is easy to use. These characteristics provide high flexibility and enable use in various locations of a hospital such as a patient's bedroom by trained personnel such as a nurse practitioner. Secondly, the portability and simple use enables implementation of monitoring brain density variations during emergency and rescue operations by, for example, a paramedic. As is evident, early detection of brain density variations and possible early diagnostic of a patient's pathological condition is highly beneficial for a patient's treatment if not life saving.

Numerous other embodiments of the invention will be apparent to persons skilled in the art without departing from the spirit and scope of the invention as defined in the appended claims.

What is claimed is:

1. A method for non-invasive monitoring of density variations of a medium, the medium substantially confined within at least a solid boundary, the method comprising:
 a) providing into the medium and for transmission therethrough at least two ultrasonic pulses having different frequencies;
 b) sensing the at least two ultrasonic pulses after traveling through the medium and providing a receive signal in dependence thereupon;
 c) processing the receive signal for determining at least two phase differences between the phases of the at least two sensed ultrasonic pulses and the phases of the at least two provided ultrasonic pulses;
 d) determining phase of at least a beat frequency in dependence upon the at least two phase differences; and,
 e) determining data indicative of a density variation of the medium based on the at least two phase differences and the phase of the at least a beat frequency.

2. A method as defined in claim 1 comprising:
 repeating the steps a) to c); and,
 determining data indicative of a density variation of the medium based on the at least two phase differences.

3. A method as defined in claim 2 wherein the receive signal is converted using a variable sampling frequency.

4. A method as defined in claim 1 comprising:
 varying the frequencies of the at least two ultrasonic pulses;
 repeating the steps a) to c); and, determining data indicative of a density variation of the medium based on the at least two phase differences.

5. A method as defined in claim 4 comprising:
 adjusting the frequencies of the at least two ultrasonic pulses such that an initial phase of the at least a beat frequency is approximately $\pi$.

6. A method as defined in claim 4 comprising:
 using a processor determining the different frequencies of the at least two ultrasonic pulses; and,
 using an ultrasonic pulse generator in communication with the processor generating the at least two ultrasonic pulses in dependence upon the determined different frequencies.

7. A method as defined in claim 6 wherein the frequencies of the at least two ultrasonic pulses are related to each other by ratios of integer numbers.

8. A method as defined in claim 7 wherein the medium is a human brain, and comprising:
 determining most responsive frequencies of the at least two ultrasonic pulses;
 correlating the most responsive frequencies to at least a pathological condition of a human brain; and,
 providing data indicative of a pathological condition of a human brain.

9. A method as defined in claim 6 comprising:
 generating a sequence of the at least two ultrasonic pulses according to predetermined parameters indicative of: number of pulses, width of each of the pulses, delay of each of the pulses, and repetition rate.

10. A method as defined in claim 1 wherein step c) comprises:
 detecting a position of each of the at least two sensed ultrasonic pulses in the receive signal.

11. A method as defined in claim 10 comprising:
determining an envelope of the receive signal; and,
detecting edges of the sensed ultrasonic pulses.

12. A method as defined in claim 10 wherein step c) comprises:
sampling data points from a center of each pulse;
transforming the sampled data points into Fourier domain;
determining the phase of each pulse using a frequency bin closest to the frequencies of the at least two provided ultrasonic pulses.

13. A method as defined in claim 12 comprising:
testing linearity of the phase of the transformed data points with respect to frequency; and,
removing erroneous data points.

14. A method as defined in claim 13 comprising:
averaging each of the at least two phase differences.

15. A method as defined in claim 1 wherein the at least two ultrasonic pulses are reflected from the at least a solid boundary.

16. A method as defined in claim 15 comprising:
performing beam steering for detecting the reflected ultrasonic pulses.

17. A method as defined in claim 1 wherein the medium is a human brain and wherein determining data comprises determining data indicative of a density variation of the human brain based on the at least two phase differences and the phase of the at least a beat frequency.

18. A method as defined in claim 17 wherein the frequencies are within a range from 0.5 MHz to 2.5 MHz.

19. An apparatus for non-invasive monitoring of brain density variations comprising:
an ultrasonic pulse generator for generating at least two ultrasonic pulses having different frequencies;
a transmitter in signal communication with the ultrasonic pulse generator for coupling the at least two ultrasonic pulses into the brain for transmission therethrough;
a sensor array probe for sensing the at least two ultrasonic pulses after traveling through the brain and for providing a receive signal in dependence thereupon;
an analog-to-digital converter in signal communication with the sensor array for converting the receive signal into digital receive signal data;
a processor in communication with the ultrasonic pulse generator, the analog-to-digital converter, and the sensor array, the processor for:
  a) providing at least a control signal to the ultrasonic pulse generator indicative of at least a parameter of the at least two ultrasonic pulses;
  b) performing beam steering for detecting the at least two ultrasonic pulses;
  c) processing the digital receive signal data for determining at least two phase differences between the phases of the at least two sensed ultrasonic pulses and the phases of the at least two provided ultrasonic pulses;
  d) determining at least a beat frequency phase in dependence upon the at least two phase differences;
  e) determining at least a density variation based on the at least two phase differences and the phase of the at least a beat frequency; and,
  f) repeating the steps a) to e) while varying the frequencies of the at least two ultrasonic pulses.

20. An apparatus for non-invasive monitoring of brain density variations as defined in claim 19 comprising non-volatile memory having stored thereupon data indicative of a plurality of pathological conditions of a human brain, the processor for:
determining most responsive frequencies of the at least two ultrasonic pulses in dependence upon the at least a density variation;
correlating the most responsive frequencies to the data indicative of a plurality of pathological conditions of a human brain; and,
providing data indicative of a pathological condition of the human brain.

21. An apparatus for non-invasive monitoring of brain density variations as defined in claim 20 comprising a user interface in communication with the processor for receiving instructions from a user and for providing at least a control signal in dependence thereupon to the processor, and for displaying the data indicative of a density variation and the data indicative of the pathological condition.

* * * * *

UNITED STATES PATENT AND TRADEMARK OFFICE
CERTIFICATE OF CORRECTION

| | | |
|---|---|---|
| PATENT NO. | : 7,854,701 B2 | Page 1 of 1 |
| APPLICATION NO. | : 10/898208 | |
| DATED | : December 21, 2010 | |
| INVENTOR(S) | : Stergios Stergiopoulos and Miroslaw Wrobel | |

It is certified that error appears in the above-identified patent and that said Letters Patent is hereby corrected as shown below:

On the title page, item [73] assignee "Stergios Stergiopoulos, Toronto, Ontario (CA)" should be changed to --HER MAJESTY THE QUEEN IN RIGHT OF CANADA AS REPRESENTED BY THE MINISTER OF NATIONAL DEFENCE, OTTAWA, ONTARIO (CA)--

Signed and Sealed this
Twelfth Day of July, 2011

David J. Kappos
*Director of the United States Patent and Trademark Office*